United States Patent [19]

Owen et al.

[11] Patent Number: 5,985,874

[45] Date of Patent: Nov. 16, 1999

[54] SUBSTITUTED MORPHOLINE DERIVATIVE AND ITS USE AS A THERAPEUTIC AGENT

[75] Inventors: Simon Neil Owen, London; Christopher John Swain, Duxford; Brian John Williams, Dunmow, all of United Kingdom

[73] Assignee: Merck Sharp & Dohme Ltd., Hoddesdon, United Kingdom

[21] Appl. No.: 09/306,957

[22] Filed: May 7, 1999

[30] Foreign Application Priority Data

May 11, 1998 [GB]  United Kingdom ................... 9810092

[51] Int. Cl.⁶ ....................... A61K 31/535; C07D 413/06
[52] U.S. Cl. ......................... 514/236.2; 544/132
[58] Field of Search .......................... 544/132; 514/236.2

[56] References Cited

U.S. PATENT DOCUMENTS 5,612,337  3/1997  Baker et al. ............................. 544/132

*Primary Examiner*—Robert W. Ramsuer
*Attorney, Agent, or Firm*—J. Eric Thies; David L. Rose

[57] ABSTRACT

The present invention relates to the compound of formula (I)

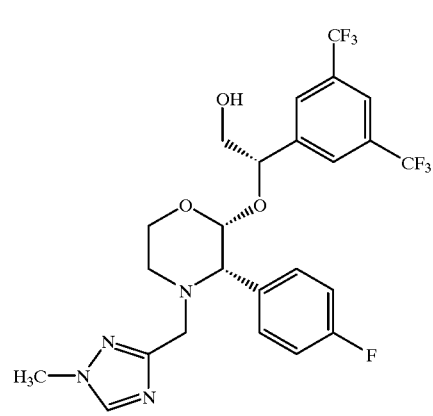

or a pharmaceutically acceptable salt thereof.

The compounds are of particular use in the treatment or prevention of pain or inflammation, migraine, emesis, postherpetic neuralgia, depression or anxiety.

6 Claims, No Drawings

SUBSTITUTED MORPHOLINE DERIVATIVE AND ITS USE AS A THERAPEUTIC AGENT

This invention relates to a novel compound which is useful as a tachykinin antagonist. More particularly, the invention relates to a novel morpholine derivative and to pharmaceutically acceptable salts thereof, to processes for its preparation, pharmaceutical compositions containing it, and to its use in medicine.

International (PCT) patent specification No. WO 95/18124 published Jul. 6th, 1995) discloses substituted morpholine derivatives as tachykinin antagonists. In particular WO 95/18124 discloses morpholine derivatives of the formula

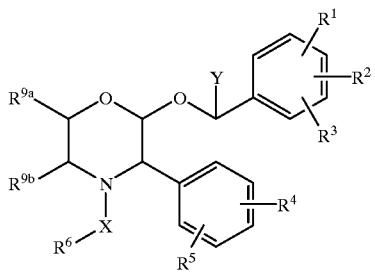

Preferred classes of compounds of this formula include inter alia compounds in which the group Y is a $CH_2OH$ group.

We have now found that the novel compound of the present invention is a potent antagonist of tachykinins, especially of substance P.

Furthermore, the compound of the present invention possesses a high degree of oral bioavailability together with high affinity for the human $NK_1$ receptor. In addition, the compound of the present invention is found to possess a rapid onset of action due to its highly desirable penetration into the central nervous system.

The present invention provides the compound of the formula (I):

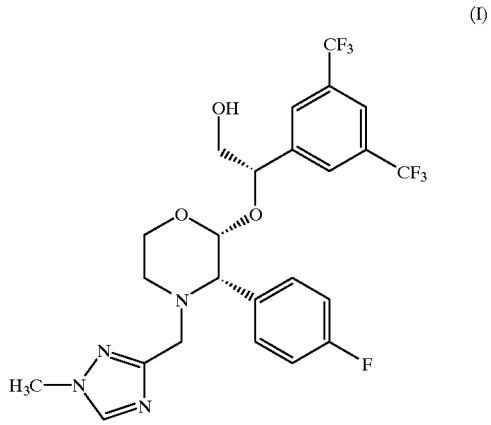

or a pharmaceutically acceptable salt thereof

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula (I) and salts thereof, for example, hydrates.

The present invention further provides pharmaceutical compositions comprising the compound of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising the compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, LipofUndin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing the compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising the compound of formula (I), which process comprises bringing the compound of formula (I) into association with a pharmaceutically acceptable carrier or excipient.

The compound of formula (I) is of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compound of formula (I) is also of value in the treatment of a combination of the above conditions, in particular in the treatment of combined post-operative pain and post-operative nausea and vomiting.

The compound of formula (I) is particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compound of formula (I) is of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compound of formula (I) is also of use in the treatment of emesis induced by radiation including radiation therapy such as in the treatment of cancer, or radiation sickness; and in the treatment of post-operative nausea and vomiting.

It will be appreciated that the compound of formula (I) may be presented together with another therapeutic agent as a combined preparation for simultaneous, separate or sequential use for the relief of emesis. Such combined preparations may be, for example, in the form of a twin pack.

A further aspect of the present invention comprises the compound of formula (I) in combination with a 5-HT$_3$ antagonist, such as ondansetron, granisetron or tropisetron, or other anti-emetic medicaments, for example, a dopamine antagonist such as metoclopramide or domperidone or GABA$_B$ receptor agonists such as baclofen. Additionally, the compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, the compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.,* (1993) 250, R5-R6, the compound of the present invention has been found to attenuate the retching and vomiting induced by cisplatin.

The compound of formula (I) is also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The compound of formula (I) is also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

The present invention further provides the compound of formula (I) for use in therapy.

According to a further or alternative aspect, the present invention provides the compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of the compound of formula (I) or a composition comprising the compound of formula (I).

According to a further aspect of the present invention, it may be desirable to treat any of the aforementioned conditions with a combination of the compound of formula (I) and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, the compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, the compound of formula (I) may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of the compound of formula (I) and an effective amount of a bronchodilator.

The present invention also provides a composition comprising the compound of formula (I), a bronchodilator, and a pharmaceutically acceptable carrier.

It will be appreciated that for the treatment or prevention of migraine, the compound of formula (I) may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, the compound of formula (I) may be used in conjunction with an antagonist of N-methyl D-aspartate (NMDA), such as dizocilpine.

For the treatment or prevention of inflammatory conditions in the lower urinary tract, especially cystitis, the compound of formula (I) may be used in conjunction with an anti-inflammatory agent such as a bradykinin receptor antagonist.

It will be appreciated that for the treatment or prevention of pain or nociception, the compound of formula (I) may be used in conjunction with other analgesics, such as acetaminophen (paracetamol), aspilin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Therefore, in a further aspect of the present invention, there is provided a pharmaceutical composition comprising the compound of formula (I) and an analgesic, together with at least one pharmaceutically acceptable carrier or excipient.

In a further or alternative aspect of the present invention, there is provided a product comprising the compound of formula (I) and an analgesic as a combined preparation for simultaneous, separate or sequential use in the treatment or prevention of pain or nociception It will be appreciated that for the treatment of depression or anxiety, the compound of formula (I) may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, $\alpha$-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising the compound of formula (I) and an anti-depressant or anti-anxiety agent, together with at least one pharmaceutically acceptable carrier or excipient.

In a further or alternative aspect of the present invention, there is provided a product comprising the compound of formula (I) and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulumia nervosa and compulsive eating disorders, the compound of formula (I) may be used in conjunction with other anorectic agents.

The present invention accordingly provides the use of the compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of the compound of formula (I) and an amount of an anorectic agent, such that together they give effective relief.

In a further aspect of the present invention, there is provided a pharmaceutical composition comprising the compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising the compound of formula (I) and an anorectic agent as a combined preparation for simultaneous, separate or sequential use in the treatment or prevention of eating disorders.

In a further embodiment of the present invention there is provided the use of the compound of formula (I) and an anorectic agent for the manufacture of a medicament for the treatment or prevention of obesity, bulimia nervosa or compulsive eating disorders.

The present invention also provides a method for the treatment or prevention of obesity, bulimia nervosa or compulsive eating disorders, which method comprises administration to a patient in need of such treatment an amount of the compound of formula (I) and an amount of an anorectic agent, such that together they give effective relief.

Suitable anorectic agents of use in combination with the compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compound of formula (I) may also be used in combination with a selective serotonin reuptake inhibitor (SSRI).

The present invention accordingly provides the use of the compound of formula (I) and an SSRI for the manufacture of a medicament for the treatment or prevention of obesity.

The present invention also provides a method for the treatment or prevention of obesity, which method comprises administration to a patient in need of such treatment an amount of the compound of formula (I) and an amount of an SSRI, such that together they give effective relief.

In a further aspect of the present invention, there is provided a pharmaceutical composition for the treatment or prevention of obesity comprising the compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising the compound of formula (I) and an SSRI as a combined preparation for simultaneous, separate or sequential use in the treatment or prevention of obesity.

Suitable selective serotonin reuptake inhibitors of use in combination with the compound of formula (I) include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($g/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

A further aspect of the present invention comprises the use of the compound of formula (I) for achieving a chronobiologic (circadian rhythm phase-shifting) effect and alleviating circadian rhythm disorders in a mammal. The present invention is further directed to the use of the compound of formula (I) for blocking the phase-shifting effects of light in a mammal.

The present invention further relates to the use of the compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of the compound of formula (I) or a pharmaceutically acceptable salt thereof.

In a preferred embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of the compound of formula (I) or a pharmaceutically acceptable salt thereof.

In another preferred embodiment, the present invention provides a method for shortening the time of reintrainment of circadian rhythms in a subject following a shift in the sleep-wake cycle which comprises administering to the subject an appropriate amount of the compound of formula (I) or a pharmaceutically acceptable salt thereof.

In a more preferred embodiment, the present invention provides a method for alleviating the effects of jet lag in a traveller, especially a mammal, which comprises administering to the traveller an alertness increasing amount of the compound of formula (I) or a pharmaceutically acceptable salt thereof. The purpose of this embodiment is to assist the body to adjust physiologically to the changes in sleep and feeding patterns when crossing several time zones.

In another more preferred embodiment, the present invention provides a method for resetting the internal circadian clock in a subject, for example shift workers changing from a day to a night shift or vice versa, which comprises administering to the subject an appropriate amount of the compound of formula (I) or a pharmaceutically acceptable salt thereof.

The present invention is further directed to the use of the compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of the compound of formula (I) or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The compound of formula (I) may be used alone or in combination with other agents which are known to be beneficial in altering circadian rhythms or in the enhancement of sleep efficiency. For example, the compound of formula (I) may be administered in conjunction with other compounds which are known in the art to be useful for suppressing or stimulating melatonin production including melatonergic agents, noradrenergic and serotonergic re-uptake blockers, alpha-1-noradrenergic agonists, monamine oxidase inhibitors, beta-adrenergic blockers and benzodiazepines, such as atenolol; or with other compounds which are known in the art to be useful for stimulating melatonin production including tricyclic antidepressants and alpha-2-adrenergic antagonists; or with melatonin precursors such as tryptophan, 5-hydroxytryptophan, serotonin and N-acetylserotonin; as well as melatonin analogues, melatonin agonists and melatonin antagonists.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The excellent pharmacological profile of the compound of formula (I) offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of disorders of the central nervous system, a suitable dosage level is about 0.001 to 25 mg/kg per day, preferably about 0.005 to 10 mg/kg per day, and especially about 0.005 to 5 mg/kg per day. The compounds may be administered (preferably orally) on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of the compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compound of formula (I) may be prepared by the reaction of a compound of formula (II) with a compound of formula (III)

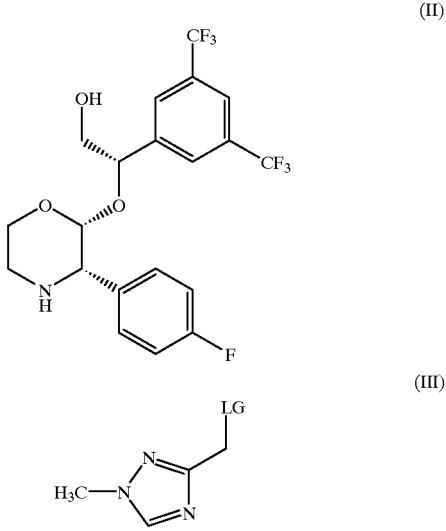

(II)

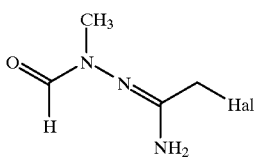

(III)

where LG is a leaving group such as an alkyl- or arylsulphonyloxy group (e.g. mesylate or tosylate) or a halogen atom (e.g. bromine, chlorine or iodine.

This reaction may be performed in conventional manner, for example in an organic solvent such as dimethylformamide in the presence of an acid acceptor such as potassium carbonate.

According to another general process (B), the compound of formula (I) may be prepared by the reaction of a compound of formula (II) with a compound of formula (IV)

(IV)

$$\underset{H}{\overset{O}{\underset{\|}{C}}}-\underset{\underset{H}{|}}{\overset{CH_3}{N}}-N=\underset{NH_2}{\overset{}{C}}-Hal$$

wherein Hal is a halogen atom, for example, bromine, chlorine or iodine (especially chlorine), in the presence of a base.

Suitable bases of use in the reaction include alkali metal carbonates such as, for example, potassium carbonate. The reaction is conveniently effected in an anhydrous solvent such as, for example, anhydrous dimethylformamide, preferably at temperatures up to about 140° C. For instance, initially at between 0° C. and 60° C., increasing to between 100° C. and 140° C.

The compound of formula (II) may be prepared using the method described in WO 95/18124 (see Description 21).

The compound of formula (III) may be prepared by conventional methods well known in the art or based upon the method described in the Examples herein.

The compounds of formula (IV) are known compounds or may be prepared by methods well known in the art (see, for instance, WO 95/18124).

During the above synthetic sequence it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The compound of this invention was tested by the methods set out at pages 36 to 39 of International Patent Specification No. WO 93/01165. The compound was found to be active with $IC_{50}$ at the $NK_1$ receptor of less than 1 nM on said test method.

The following non-limiting Examples serve to illustrate the preparation of the compound of the present invention:

DESCRIPTION 1

1-Formyl-1-methylhydrazine

A solution of methylhydrazine (53 ml, 1.0 mol) in methanol (300 ml) was cooled (0° C.) and a solution of methyl formate (64 ml, 1.04 mol) in methanol (100 ml) was added dropwise such that the internal temperature did not exceed 5° C. The mixture was allowed to warm to room temperature and left for 2 hours. The methanol was removed in vacuo and the residue purified by vacuum distillation (bp 70° C. at 2 mbar) to give the title compound (73.7 g, 99% yield). $^1$H-NMR (250 MHz, CDCl$_3$) (a mixture of two rotamers 1:2) δ 8.26(0.3H, s, C(O)H), 8.00(0.7H, s, C(O)H), 4.31 (0.8H, s, NH$_2$), 3.94(1.2H, s, NH$_2$), 3.13(2.0H, s, NCH$_3$), 3.12(1.0H, s, NCH$_3$).

DESCRIPTION 2

3-Chloromethyl-1-methyl-1,2,4-triazole hydrochloride

To a cooled (−5° C.) solution of chloroacetonitrifle (27 ml, 0.43 mol) in dry methanol (27 ml) was added sodium methoxide in methanol (0.3M, 42 ml) dropwise such that the internal temperature did not exceed 0° C. The solution was then allowed to warm to room temperature and left for 45 minutes before acetic acid (0.75 ml, 13 mmol) was added and the mixture recooled (0° C). A solution of 1-formyl-1-methylhydrazine (30.5 g, 0.412 mol) in dry methanol (15 ml) was added such that the internal temperature did not exceed 0° C. and the yellow solution was allowed to warm to room temperature before removing the methanol in vacuo. This solution was added portionwise to a cooled (4° C.) solution of phosphorus oxychloride (200 ml, 2.1 mol) in chlorobenzene (600 ml) and the mixture allowed to warm to room temperature and left for 1 hour. The mixture was slowly heated to 60° C. until the effervescence had subsided and then the solution was heated under reflux for 3 hours before cooling. The POCl$_3$ and chlorobenzene were removed in vacuo and the residue was azeotroped (x3) with toluene. The residue was neutralized with aqueous sodium carbonate and partitioned between aqueous sodium carbonate (500 ml) and dichloromethane (500 ml). The aqueous layer was extracted (x3) with dichloromethane, the organic phases were combined, dried MgSO$_4$) and reduced in vacuo. The residue was purified by flash silica gel chromatography eluting with 1 to 5% methanol in dichloromethane to give 43.3 g of the free base of the title compound. To a solution of the residue in diethyl ether was added a solution of 1M HCl in diethyl ether (329 ml), evaporated to dryness and the resultant solid recrystallised (ethyl acetate/methanol) to give the title compound (39 g, 54% yield, mp 105–107° C). $^1$H-NMR (250 MHz, DMSO-d$_6$) δ 8.51(1H, s, N=CHN), 4.71(2H, s, CH$_2$Cl), 3.86(3H, s, NCH$_3$).

EXAMPLE 1

2(R)-(1-(3,5-Bis(trifluoromethyl)phenyl)-2(S)-hydroxyethoxy)-3(S)-(4-fluorophenyl)-4-((1-methyl-1,2,4-triazol-3-yl)methylene)morpholine To a solution of 2(R)-(1-(3,5-bis(trifuoromethyl)phenyl)-2(S)-hydroxyethoxy)-3(S)-(4-fluorophenyl)morpholine (prepared according to the method described in International Patent Specification No. WO 95/18124; 11.7 g, 29 mmol) in N,N-dimethylformamide (75 ml) was added 3-chloromethyl-1-methyl-1,2,4-triazole hydrochloride (6.5 g, 39 mmol) and potassium carbonate (17.8 g, 129 mmol). The mixture was heated (100° C.) under an atmosphere of nitrogen for 16 h when additional 3-chloromethyl-1-methyl-1,2,4-triazole hydrochloride (2.1 g, 12.5 mmol) was added and the heating continued (100° C.) for 20 hours. After cooling, the N,N-dimethylformamide was removed in vacuo and the residue was partitioned between ethyl acetate (500 ml) and water (600 ml). The aqueous phase was extracted with ethyl acetate (2×500 ml), the organic phases combined and washed with saturated brine (0.5 liters) and dried ($MgSO_4$). The organic phase was reduced in vacuo to dryness and the residue was purified by flash chromatography, eluting with 4% to 6% methanol in ethyl acetate to give the title compound (9.93 g, 70% yield). $^1$H-NMR (360 MHz, $CDCl_3$) δ 7.96(1H, s, N=CHN), 7.67(1H, s, ($CF_3$)CCHC($CF_3$)), 7.51(2H, broad dd, (C)CC(H)C(H)), 7.16(2H, s, ($CF_3$)CCHC(C)), 7.07(2H, dd, J 8.7 Hz and 8.7 Hz, CHCFCH), 4.87(1H, dd, J 7.2 Hz and 4.1 Hz, OC($CH_2$OH)(H)C), 4.42(1H, d, J 2.8 Hz, OC(H)0), 4.34 (1H, td, J 11.7 Hz and 2.5 Hz, $OCH_1H_2CH_2$), 3.88(3H, s, $NCH_3$), 3.80(1H, d, J 14.0 Hz, $NCH_1H_2$CH(=N)(N)), 3.67–3.48(4H, m), 3.25(1H, d, J 14.0 Hz, $NCH_1H_2$CH(=N)(N)), 2.99(1H, d, J 11.8 Hz, $NCH_1H_2CH_2$), 2.58(1H, td, J 11.9 Hz and 3.6 Hz, $NCH_1H_2CH_2$), m/z ($ES^+$) 549 (M+H, 100%), HPLC (50% MeCN in 25 mM $KH_2PO_4$/0.2% triethylamine, pH 3.0, 1 ml/min, LUNA (150×4.6 mm), UV 210 nm)>99.5% purity.

What is claimed is:

1. The compound of the formula (I):

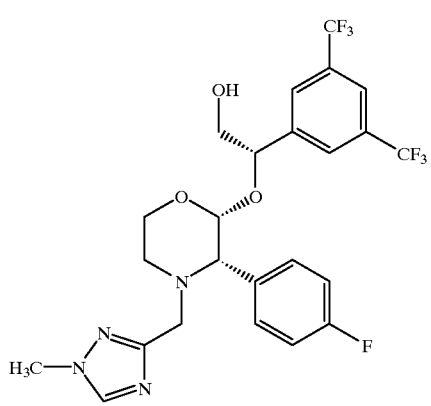

(I)

or a pharmaceutically acceptable salt thereof.

2. The compound as claimed in claim 1 in the form of a pharmaceutically acceptable acid addition salt.

3. A pharmaceutical composition comprising a compound as claimed in claim 1, together with at least one pharmaceutically acceptable carrier or excipient.

4. A method for the treatment or prevention of physiological disorders associated with an excess of tachykinins, which method comprises administration to a patient in need thereof of a tachykinin reducing amount of a compound according to claim 1.

5. A method according to claim 4 for the treatment or prevention of pain or inflammation, migraine, emesis, postherpetic neuralgia, depression or anxiety.

6. A process for the preparation of a compound as claimed in claim 1 which comprises:

(A) reacting a compound of formula (II) with a compound of formula (III):

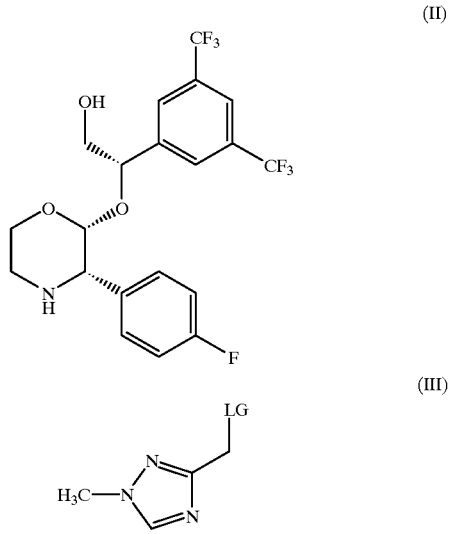

where LG is a leaving group; or (B) reacting a compound of formula (I) with a compound of formula (IV):

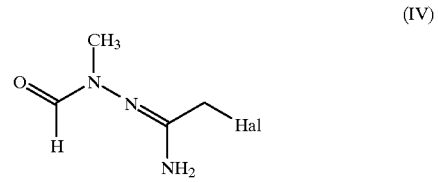

wherein Hal is a halogen atom, the presence of a base;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *